United States Patent [19]

Poole et al.

[11] Patent Number: 4,624,248
[45] Date of Patent: * Nov. 25, 1986

[54] TRANSPARENT PRESSURE GARMENT

[75] Inventors: Forrest R. Poole, Worcester; David G. Hansen, Sterling, both of Mass.

[73] Assignee: David Clark Company Incorporated, Worcester, Mass.

[*] Notice: The portion of the term of this patent subsequent to Jul. 30, 2002 has been disclaimed.

[21] Appl. No.: 720,585

[22] Filed: Apr. 8, 1985

Related U.S. Application Data

[63] Continuation of Ser. No. 464,662, Feb. 7, 1983, Pat. No. 4,531,516.

[51] Int. Cl.⁴ ............................................. A61F 5/04
[52] U.S. Cl. ................................. 128/89 R; 128/87 R; 128/DIG. 20; 128/128; 128/327
[58] Field of Search ............... 128/89 R, 327, 87 R, 128/90, DIG. 20, 118

[56] References Cited

U.S. PATENT DOCUMENTS

| | | | |
|---|---|---|---|
| 3,083,708 | 4/1963 | Gottfried | 128/DIG. 20 |
| 3,332,415 | 7/1967 | Ericson | 128/DIG. 20 |
| 3,454,010 | 7/1968 | Lilligren et al. | 128/327 |
| 3,785,375 | 1/1974 | Lipson | 128/DIG. 20 |
| 3,933,150 | 1/1976 | Kaplan et al. | 128/DIG. 20 |
| 4,039,039 | 8/1977 | Gottfried | 128/DIG. 20 |
| 4,157,713 | 6/1979 | Clarey | 128/DIG. 20 |
| 4,169,467 | 10/1979 | Rabischong et al. | 128/DIG. 20 |
| 4,202,325 | 5/1980 | Villari et al. | 128/DIG. 20 |
| 4,270,527 | 6/1981 | Peters et al. | 128/DIG. 20 |
| 4,531,516 | 7/1985 | Poole et al. | 128/89 R |

*Primary Examiner*—Gene Mancene
*Assistant Examiner*—C. W. Shedd
*Attorney, Agent, or Firm*—Maurice E. Gauthier

[57] ABSTRACT

A pressure garment has a transparent exterior panel with a pair of lower sections adapted to be operatively positioned around the legs of the wearer, and with an upper section adapted to be positioned around the abdomen of the wearer. Transparent inner panels cooperate with each of the exterior panel sections to define pressure chambers therebetween. A pressurized gas such as for example compressed air, is introduced into the pressure chambers in order to inflate the same and apply pressure to the wearer's body.

6 Claims, 6 Drawing Figures

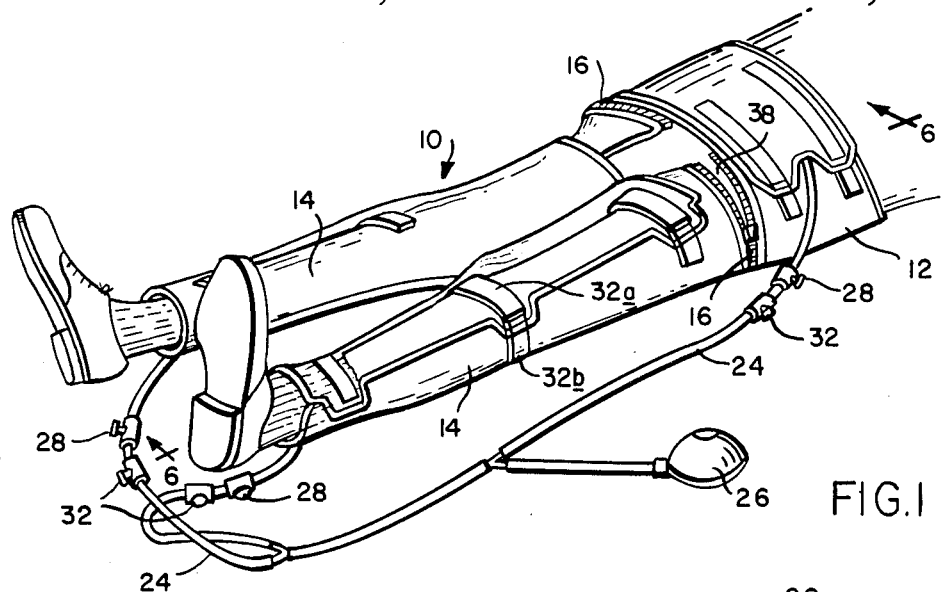
FIG.1
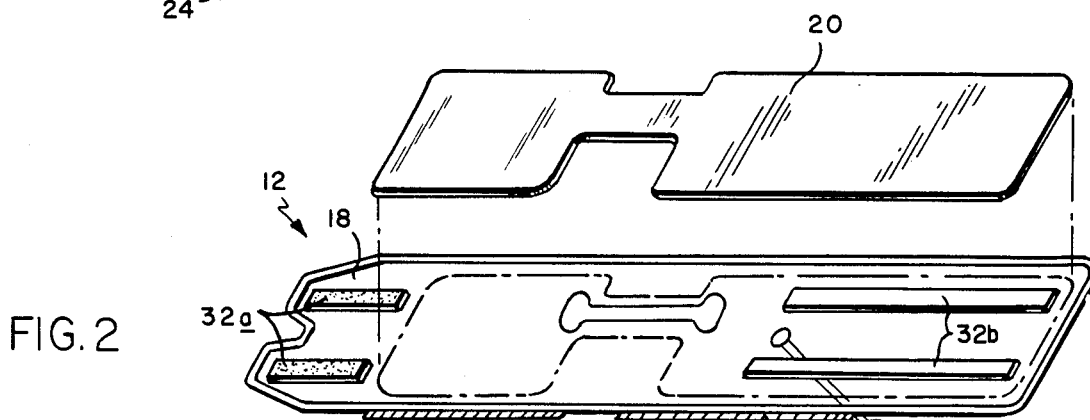
FIG.2
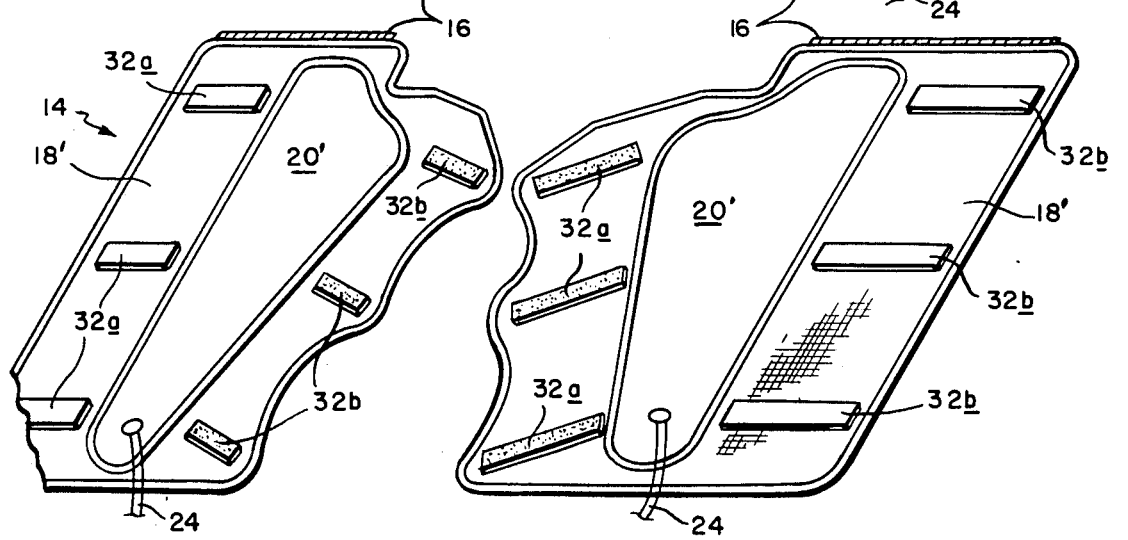

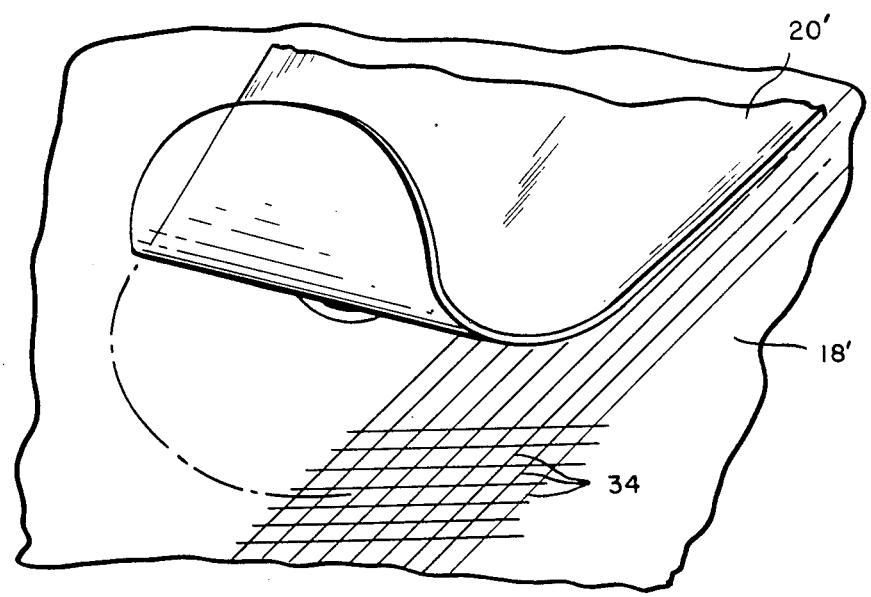
FIG.3
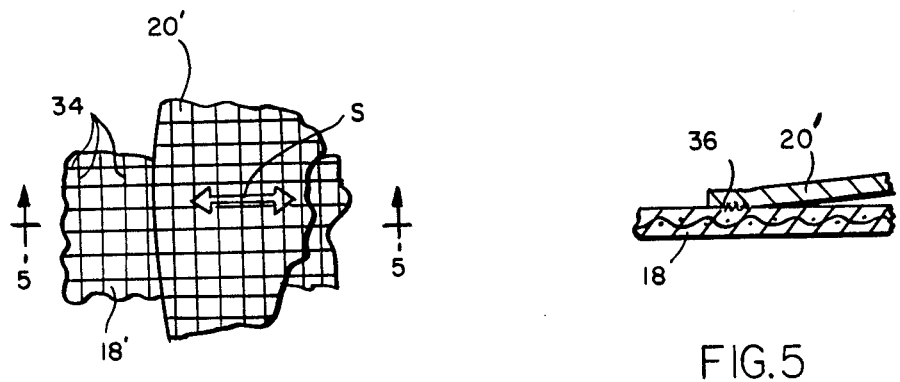
FIG.4
FIG.5
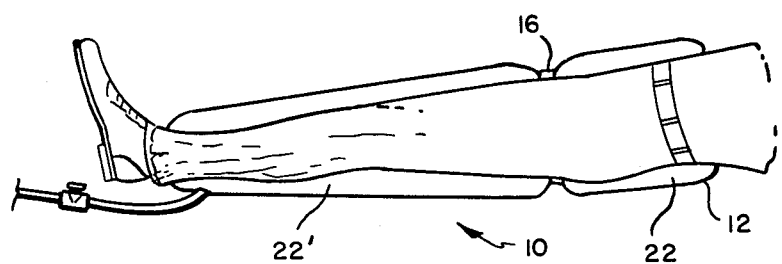
FIG.6

TRANSPARENT PRESSURE GARMENT

This is a continuation of co-pending application Ser. No. 464,662 filed on Feb. 7, 1983, now U.S. Pat. No. 4,531,516.

BACKGROUND OF THE INVENTION

1. Field of the Invention

This invention relates to inflatable garments of the type employed under emergency conditions by ambulance personnel, paramedics and the like to correct or counteract internal bleeding conditions and hypovolemia by developing an encircling pressure around the legs and abdomen of a victim.

2. Description of the Prior Art

Inflatable garments of the type referred to above are now well known and widely employed by emergency medical personnel. An example of one such garment is described in U.S. Pat. No. 3,933,150 to Kaplan et al. Here, the garment materials are opaque, and hence once the garment is applied to a victim's body, it becomes impossible to locate or examine underlying wounds or to monitor the victim's skin condition. Thus, when a victim arrives at a treatment facility, such as for example a hospital emergency room, attending personnel must first deflate and open the garment before they can begin making decisions on initial treatment steps.

Such garments also are provided conventionally with a unitary structure. Thus, if one part of the garment becomes damaged, the entire garment must be replaced at a considerable cost to the user. Moreover, the conventional unitary construction makes it difficult if not impossible to gain access to critical arteries without first deflating and opening the garment.

SUMMARY OF THE PRESENT INVENTION

The present invention comprises an improved inflatable garment having novel features which obviate or at least substantially minimize the above-noted shortcomings of conventional garments. One such novel feature lies in the fact that the garment parts are fabricated from transparent materials, thereby allowing the covered areas of a victim's body to remain in sight after the garment has been applied and inflated. This allows attending medical personnel to view underlying wounded areas as well as to monitor the victim's skin condition, and to make prompt judgments as to how and where care should be effected, without first having to deflate and remove the garment.

Another novel feature of the present invention lies in the subdivision of the garment into modular sections which are interconnected by readily separable means such as for example conventional zippers. This allows damaged sections to be replaced without having to replace the entire garment. The zippers also can be opened while the garment remains inflated, thereby allowing attending personnel to gain access to critical arteries without disturbing the application of pressure to the victim's body.

Preferably, the modular sections are fabricated from inner and outer pliable transparent panels which are sealingly joined to define inflatable pressure chambers therebetween. The outer panels are preferably reinforced with an embedded reinforcing mesh which resists distortion under presure. As compared to the outer panels, the inner panels are more pliable and thus capable of more easily conforming to the contour of the victim's body.

These and other features, objects and advantages of the present invention will be described in more detail in connection with the accompanying drawings, wherein:

BRIEF DESCRIPTION OF THE DRAWINGS

FIG. 1 is a view in perspective of a pressure garment in accordance with the present invention, showing its application to the body of a victim, with one of the zipper connections being partially opened;

FIG. 2 is an exploded perspective view of the pressure garment;

FIG. 3 is an enlarged perspective view of two cooperating garment panels, one being partially separated from the other;

FIG. 4 is an enlarged plan view of a seam portion;

FIG. 5 is a sectional view taken along line 5—5 of FIG. 4; and

FIG. 6 is a sectional view taken along line 6—6 of FIG. 1.

DETAILED DESCRIPTION

Referring now to the drawings, 10 designates a garment in accordance with the present invention. The garment has an upper section 12 adapted to be operatively positioned around the wearer's abdomen, and a pair of lower sections 14 adapted to be similarly positioned around the wearer's legs.

As can be best seen in FIG. 2, the sections 12 and 14 comprise separable modules which are detachably interconnected by mating zipper components 16. The upper abdomen section 12 consists of a transparent exterior panel 18 of elongated generally rectangular shape, and a transparent inner panel 20 which is sealingly secured around its edge to the inside surface of the outer panel. The panels 18, 20 cooperate in defining a pressure chamber 22 therebetween.

The leg sections 14 are similarly made up of exterior and interior panels 18', 20' sealingly interconnected to define pressure chambers 22' therebetween. The chambers 22 and 22' are connected via hose segments 24 to a pump 26 or other like source of pressurized gas. The hose segments 24 are provided with conventional automatic pressure relief valves 28 and manual shut-off valves 32.

The respective sections 12 and 14 each have fastening means which typically can comprise strips 32a and 32b of "Velcro" on the interior and exterior surfaces respectively.

The sections 12 and 14 are each fabricated from essentially the same materials. Thus, as can best be seen in FIGS. 3–5 which illustrate a typical leg section 14, the outer panel will comprise a pliable transparent plastic material having a reinforcing scrim or mesh 34 embedded therein. An example of one such material is a laminated urethane film marketed under the trademark "HI-TUFF" by J. P Stevens & Co., Inc. The mesh has interwoven warp and woof filaments, with either the warp or woof filaments being oriented in a substantially parallel relation with respect to the direction of stress (shown at "S" in Figure imposed on the exterior panel as a result of the pressure chamber being inflated. The inner panels 20, 20' are of an unreinforced transparent urethane film having a pliability which is greater than that of the outer reinforced panels 18, 18'. With this arrangement, the outer reinforced panels resist deformation and thus maintain the overall shape of the garment, whereas the inner panels conform more readily to the contours of the victim's body. As shown for example in FIG. 5, the inner and outer panels are sealingly secured to each other as at In light of the foregoing, it will now be understood by those skilled in the art that the present invention offers a number of significant advantages over conventional inflatable garments. Of primary importance, as illustrated in FIG. 1, is the fact that the underlying areas of the victim's body remain visible after the garment has been applied and inflated. Thus, attending medical personnel can observe injuries and monitor skin conditions without having to deflate and remove the garment.

As also shown in FIG. 1, the zipper connections 16 are designed to be opened to allow medical personnel to gain access to critical arteries located for example at 38. Here again, this can be accomplished without first having to deflate and remove the garment.

Although the garment is transparent, its outer panels are fully reinforced against distortion under pressure. However, the inner panels are sufficiently pliable so as to conform to the contours of the victim's body. The zipper connections 16 allow for easy replacement of damaged modular components, without having to scrap the entire garment.

We claim:

1. A modular pressure garment comprising: three separate transparent exterior panels, three separate transparent interior panels, each of said interior panels being joined peripherally to a respective one of said exterior panels to form three separate inflatable chambers, the exterior panels having at least some of their peripheral portions extending beyond the peripheries of their associated interior panels, one of said exterior panels being dimensioned and configured to be operatively applied at a position encircling the abdomen of the wearer, and each of the other two of said exterior panels being dimensioned and configured to be operatively applied at a position encircling a leg of the wearer; each of the thus operatively applied exterior panels having its associated interior panel facing inwardly and having overlapping peripheral portions, the transparency of said interior and exterior panels providing a substantially unhindered view therethrough; means for detachably interconnecting the overlapping peripheral portions of said exterior panels; and means for inflating said chambers.

2. The pressure garment of claim 1 wherein said inner panels are more pliable than said exterior panels.

3. The pressure garment of claim 1 wherein said exterior panels are provided with a reinforcing mesh embedded therein.

4. The pressure garment of claim 3 wherein said mesh includes interwoven warp and woof filaments, with one of either said warp or woof filaments being oriented in substantially parallel relationship to the direction of stress imposed on said exterior panels as a result of said units being inflated.

5. The pressure garment of either claims 2, 3 or 4 wherein said inflatable units are detachably interconnected.

6. The pressure garment of claim 5 wherein slide fasteners are employed to detachably interconnect said inflatable units, said slide fasteners being arranged to enable said garment to be opened at the juncture between the unit covering the wearer's abdomen and the units covering the wearer's legs in order to gain access to the underlying area of the wearer's body while said units remain inflated.

* * * * *